United States Patent [19]

Malone

[11] 4,145,765
[45] Mar. 27, 1979

[54] SHOCK ABSORBING MOBILE ADAPTER

[76] Inventor: James F. Malone, 2830 Buena Vista St., Bakersfield, Calif. 93304

[21] Appl. No.: 815,926

[22] Filed: Jul. 15, 1977

[51] Int. Cl.² .................................................. A61F 1/04
[52] U.S. Cl. ...................................... 3/7; 244/100 R; 244/138 R; 267/60
[58] Field of Search .................. 3/7, 8, 1.2, 1, 6.1, 3/35, 30; 244/100 R, 138 R; 35/34; 248/358 AA, 399, 163; 52/DIG. 10; 135/15 PQ, 3 R; 267/60, 166

[56] References Cited

U.S. PATENT DOCUMENTS

| 1,668,122 | 5/1928 | Mummert et al. ............... 244/100 R |
| 2,478,721 | 8/1949 | Stewart ...................................... 3/1.2 |
| 2,759,739 | 8/1956 | Walsh ........................... 244/100 R X |
| 2,803,088 | 8/1957 | Swann ........................... 52/DIG. 10 |
| 2,970,388 | 2/1961 | Yonkers ........................ 52/DIG. 10 |
| 3,228,492 | 1/1966 | Blumrich ..................... 244/138 R X |
| 3,387,805 | 6/1968 | Barnett et al. ............... 244/100 R X |
| 3,754,286 | 8/1973 | Ryan .............................................. 3/7 X |
| 4,069,832 | 1/1978 | Bingham ............................... 135/3 R |

FOREIGN PATENT DOCUMENTS

| 453191 | 12/1948 | Canada ..................................... 267/60 |
| 1003618 | 2/1957 | Fed. Rep. of Germany ............ 267/60 |
| 252667 | 4/1927 | Italy .......................................... 267/60 |
| 1086154 | 10/1967 | United Kingdom .................. 135/3 R |

*Primary Examiner*—Clifford D. Crowder
*Attorney, Agent, or Firm*—Robert Charles Hill

[57] ABSTRACT

A shock absorbing mobile adapter is provided with four members in spaced apart relationship and six shock absorbing arms connecting each member to the other three members and forming an irregular tetrahedron.

5 Claims, 5 Drawing Figures

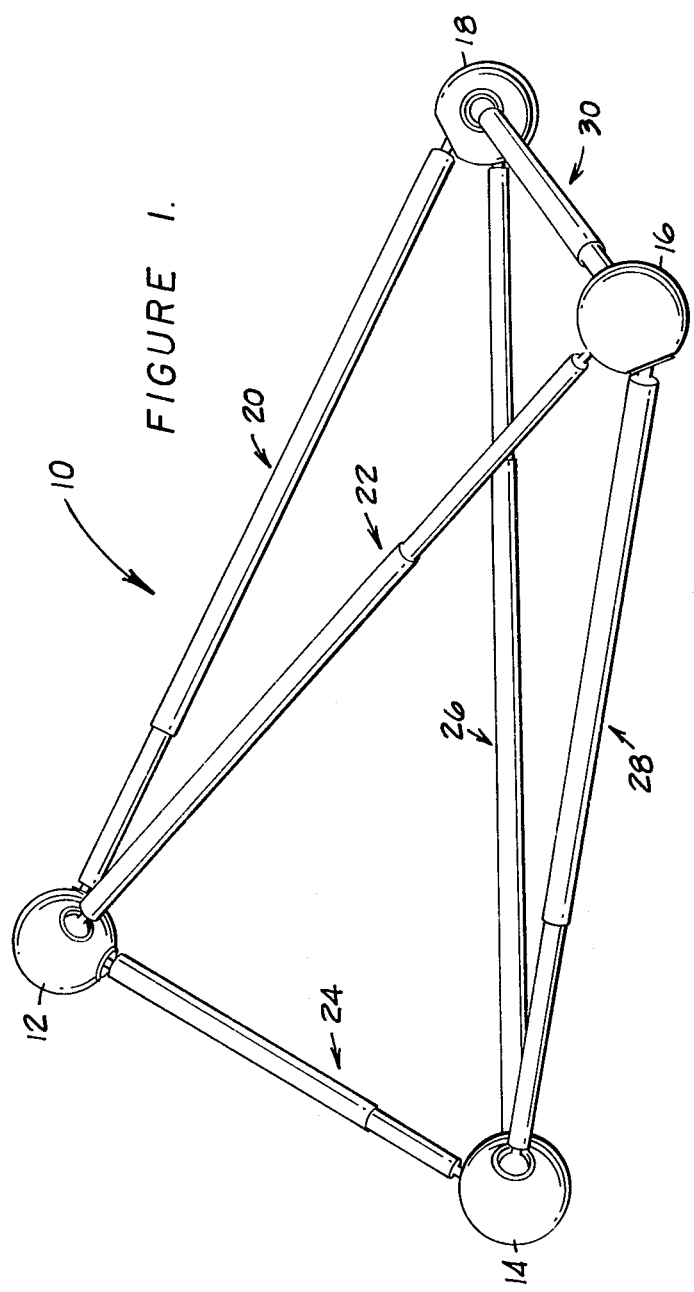
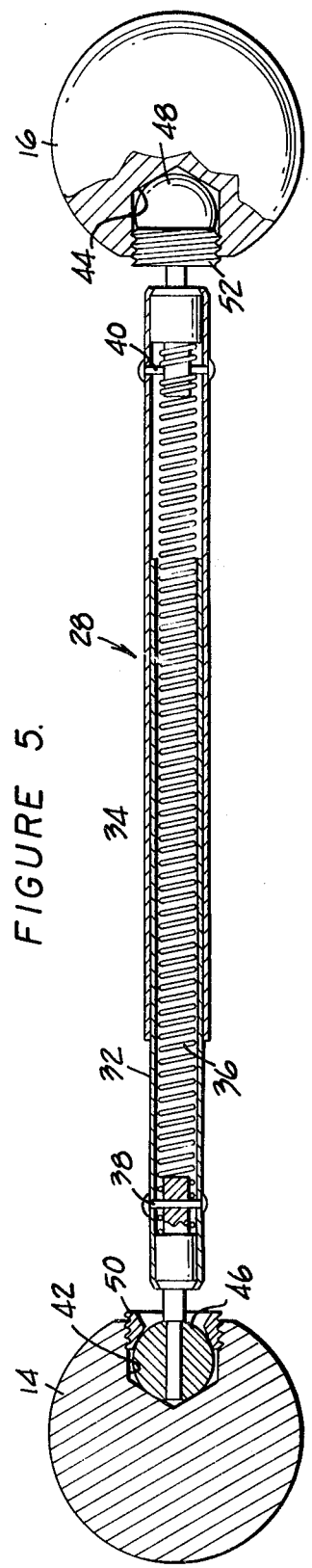

4,145,765

SHOCK ABSORBING MOBILE ADAPTER

SUMMARY OF THE INVENTION

The present invention relates to a shock absorbing mobile adapter which duplicates the gross changes in the shape of the human foot during gait. Four spheres representing stress points are interconnected by movable arms which can expand as well as contract.

BACKGROUND OF THE INVENTION

The present invention relates to a shock absorbing mobile adapter which can be used as a landing gear for cargo delivered by parachute, a prosthetic human foot, a teaching device to students learning about the motions and stresses of the foot, and as a landing device for aerospace vehicles.

The function of normal walking results in contraction, expansion and torsion of the foot. Any artificial foot should perform likewise. Careful analysis of the problems encountered with the existing prior art devices led to the conclusion that the ideal prosthetic foot should produce a dynamic object which can proceed through all the gross mechanical motions observed in the human foot during the gait cycle. This requires three plane motion. Unfortunately, as will be seen below, none of the prior art devices possesses these desired attributes.

U.S. Pat. No. 1,319,471 shows an artificial foot with a number of hinged members but without any means for lateral expansion and contraction or torsion.

U.S. Pat Nos. 2,470,480 and 2,483,506 illustrate artificial limbs which also have only single plane movement.

The present invention eliminates all of the problems inherent in the above described devices. The present invention provides three dimensional motion to facilitate easy accommodation to average ground terrain and to accept the torque of the leg on the foot in gait.

OBJECTS OF THE INVENTION

It is the primary object of the present invention to provide a new and improved shock absorbing mobile adapter.

Another object is to provide a shock absorbing mobile adapter which has three dimensional movement.

A further object is to provide structure which is inexpensive to manufacture and long lasting in usage.

BRIEF DESCRIPTION OF THE DRAWINGS

FIG. 1 is a perspective view of the shock absorbing mobile adapter of the present invention.

FIG. 5 is an enlarged cross-sectional view illustrating a shock absorbing arm interconnecting two spheres.

DESCRIPTION OF THE PREFERRED EMBODIMENT

Figure 2:
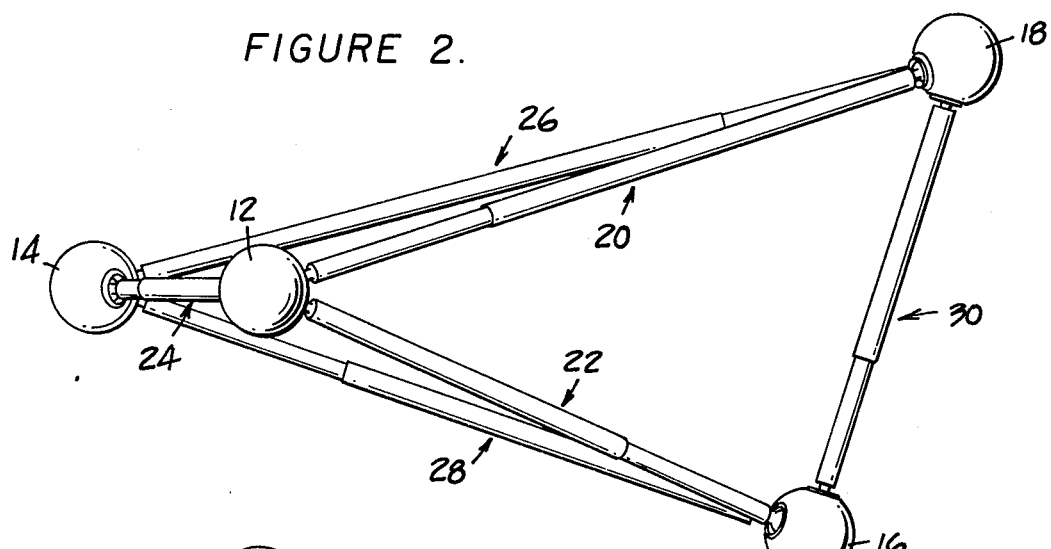
FIG. 2 is a top view of the shock absorbing mobile adapter.
Figure 3:
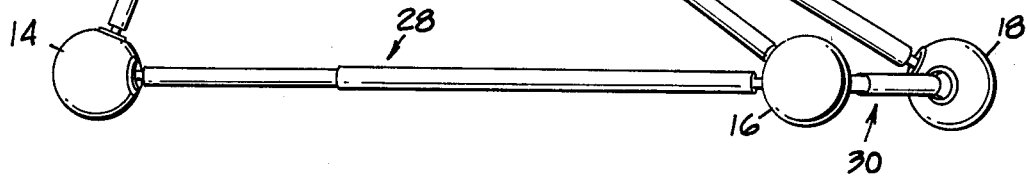
FIG. 3 is a side view of the shock absorbing mobile adapter.
Figure 4:
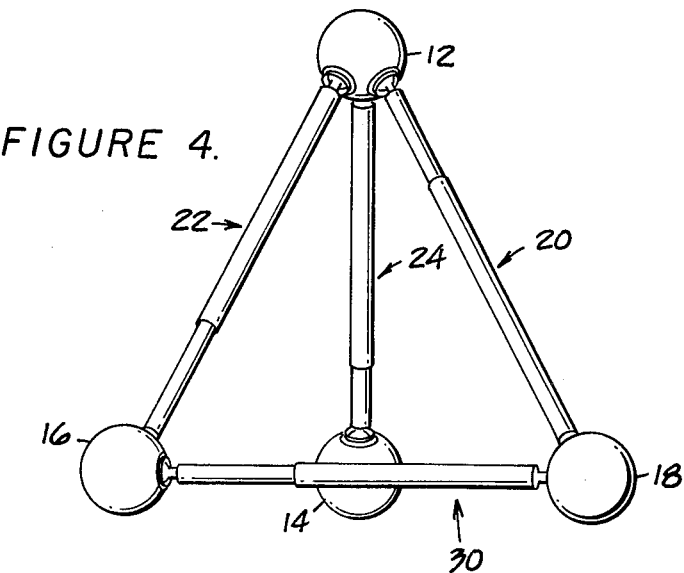
FIG. 4 is a front view of the shock absorbing mobile adapter.

Referring to FIGS. 1 through 4 of the drawings, there is shown the shock absorbing mobile adapter of this invention, generally indicated 10, which is suitable for many uses, one of which is as a prosthetic human foot. The shock absorbing mobile adapter 10 has four spherical members 12, 14, 16 and 18 in spaced apart relationship. Six shock absorbing arms, generally indicated 20, 22, 24, 26, 28 and 30, interconnect the members 12, 14, 16 and 18 to form an irregular tetrahedron.

While all the arms 20, 22, 24, 26, 28 and 30 are not obviously the same length, they all have the same internal structure which is shown in FIG. 5. Arm 28 is formed by inner tubular section 32 having a smaller width than outer tubular section 34. The sections 32 and 34 slidably telescope into each other and surround spring 36 which is secured to sections 32 and 34 by pins 38 and 40, respectively, or any other suitable means. Thus, the arms are spring loaded and capable of expansion and contraction. In fact, the spring 36 should be such that the arms can contract to at least three-fourths of its original length and expand to at least one and one-half times its original length.

As seen in FIG. 1, each spherical member 12, 14, 16 and 18 has three sockets therein. Referring now to FIG. 5, one of the sockets of member 14 is numbered 42 and one of the sockets of member 16 is numbered 44. Attached to the ends of arm 28 are globes 46 and 48 which are maintained within sockets 42 and 44 by threaded retainers 50 and 52 respectively. It can thus be seen that for the shock absorbing mobile adapter 10 twelve globes fit into and are retained within twelve sockets to form an irregular tetrahedron.

When the shock absorbing mobile adapter 10 is used as a prosthetic human foot or as a teaching device member 12 represents the talar dome, member 14 the medial and lateral tubercles of the calcaneus or heel bone, member 18 of the first metatarsal head and member 16 the fifth metatarsal head, thus illustrating the right foot. Of course, the adapter 10 can also be constructed to represent the left foot.

It is well-known that the lower extremity (thigh and leg) produces a torque during the gait cycle which is transferred to the foot when the foot is in contact with the ground. As this happens, a regular pattern of distortion appears in the overall shape of the foot, which distortion is duplicated by the shock absorbing mobile adapter 10. These motions are classified as heel contact, mid-stance (lateral and medial) and propulsion and result in members 12, 14, 16 and 18 changing position with respect to each other in order to stabilize the foot.

At heel contact, arm 24 contracts while arm 20 expands. During mid-stance lateral contact arm 28 expands while arm 22 contracts. With medial contact of mid-stance, arms 26 and 30 expand and arm 22 contracts. Propulsion results in expansion of arm 22 and contraction of arms 26 and 30. Although not a part of the present invention, the adapter 10 when used as a prosthetic human foot can be attached to the human body in a number of ways well-known in the art.

One series of approximate arm dimensions with the adapter 10 at rest which has proved to be extremely operable has arm 20 at 9.90 inches, arm 22 at 8.24 inches, arm 24 at 4.76 inches, arm 26 at 10.20 inches, arm 28 at 8.40 inches, and arm 30 at 4.50 inches.

The adapter 10 can be constructed of any material capable of withstanding the stresses of the particular desired use. For example, a teaching model can be easily constructed of aluminum.

It will be obvious that numerous modifications and variations are possible for the above described shock absorbing mobile adapter within the scope of the present invention. The foregoing description, as setting forth various constructional and operational details for purposes of and understanding of the invention only, is not to be taken as limiting the scope of the present invention which is defined only by the following claims.

I claim:

1. A shock absorbing mobile adapter, comprising:
   (a) four members in spaced apart relationship;
   (b) each member having three sockets therein;
   (c) six movable arms having a globe at each end thereof;
   (d) said twelve globes fitting within said twelve sockets forming an irregular tetrahedron whereby said adapter duplicates the gross changes in the shape of the human foot during gait.

2. The shock absorbing mobile adapter of claim 1 wherein threaded members retain the globes within the sockets.

3. The shock absorbing mobile adapter of claim 2 wherein the arms have inner and outer tubular telescoping sections.

4. The shock absorbing mobile adapter of claim 3 wherein springs are located within each arm.

5. The shock absorbing mobile adapter of claim 4 wherein the springs are secured to the arms by pins.

* * * * *